United States Patent
Schladetzky et al.

[11] Patent Number: 6,087,374
[45] Date of Patent: Jul. 11, 2000

[54] ANTI-VIRAL COMPOUNDS

[75] Inventors: Kurt D. Schladetzky, West Lafayette; Wayne A. Spitzer; Michael S. Vannieuwenhze, both of Indianapolis, all of Ind.

[73] Assignee: Eli Lilly and Company, Indianapolis, Ind.

[21] Appl. No.: 09/341,054

[22] PCT Filed: Jan. 20, 1998

[86] PCT No.: PCT/US98/01030

§ 371 Date: Jul. 2, 1999

§ 102(e) Date: Jul. 2, 1999

[87] PCT Pub. No.: WO98/31363

PCT Pub. Date: Jul. 23, 1998

Related U.S. Application Data

[60] Provisional application No. 60/035,426, Jan. 22, 1997.

[51] Int. Cl.[7] .......................... A61K 31/437; A61P 31/16; C07D 471/04
[52] U.S. Cl. ............................................. 514/303; 546/118
[58] Field of Search .............................. 546/118; 514/303

[56] References Cited

U.S. PATENT DOCUMENTS

| | | | |
|---|---|---|---|
| 4,150,025 | 4/1979 | Shimada et al. | 546/99 |
| 4,174,454 | 11/1979 | Paget et al. | 548/306 |
| 4,230,868 | 10/1980 | Paget et al. | 548/306 |
| 4,401,817 | 8/1983 | Paget et al. | 548/136 |
| 4,420,479 | 12/1983 | Morwick et al. | 424/246 |
| 4,492,708 | 1/1985 | Spitzer | 424/273 |
| 5,216,003 | 6/1993 | Vazquez | 514/381 |
| 5,545,653 | 8/1996 | Miller et al. | 514/388 |
| 5,612,360 | 3/1997 | Boyd et al. | 514/381 |
| 5,693,661 | 12/1997 | Miller et al. | 514/388 |
| 5,821,242 | 10/1998 | Colacino et al. | 514/227.2 |
| 5,891,874 | 4/1999 | Colacino et al. | 514/234.5 |

FOREIGN PATENT DOCUMENTS

| | | | |
|---|---|---|---|
| WO 97/46237 | 12/1997 | WIPO | C07D 235/30 |
| WO 98/55120 | 12/1998 | WIPO | C07D 235/30 |

*Primary Examiner*—Evelyn Mei Huang
*Attorney, Agent, or Firm*—Arlene K. Musser

[57] ABSTRACT

The present invention relates to compounds of Formula (I), or a pharmaceutically acceptable salt thereof. These compounds inhibit the growth of piconaviruses, such as rhinoviruses, Hepatitus viruses, cardioviruses, polioviruses, enteroviruses, coxsackieviruses of the A and B groups, echo virus and Mengo virus.

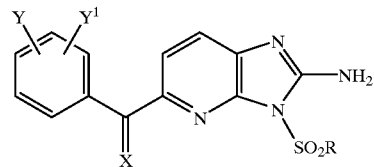

(I)

8 Claims, No Drawings

ANTI-VIRAL COMPOUNDS

This application is the National Phase of PCT/US98/01030, filed on Jan. 20, 1998, which claims the benefit of Provisional Application 60/035426, filed on Jan. 22, 1997.

FIELD OF THE INVENTION

The present invention relates to the fields of pharmaceutical and medicinal chemistry

BACKGROUND OF THE INVENTION

The incidence of viral upper respiratory disease, the common cold, is immense. It has been estimated that nearly a billion cases annually appear in the United States alone. Rhinovirus, a member of the picornaviridae family, is the major cause of the common cold in humans. Since more than 110 strains of rhinovirus have been identified, the development of a comprehensive rhinovirus vaccine is not practical. Accordingly, chemotherapy appears to be a more desirable approach. Another member of the picornavirus family is the enterovirus, which includes approximately eighty human pathogens. Many of these enteroviruses cause cold-like symptoms; others can cause more serious diseases such as polio, conjunctivitis, aseptic meningitis and myocarditis.

Illness related to rhinovirus infection is evidenced by nasal discharge and obstruction. Furthermore, it has been implicated in otitis media, predisposes the development of bronchitis, exacerbates sinusitis, and has been implicated in the precipitation of asthmatic disease. Although it is considered by many to be a mere nuisance, its frequent occurrence in otherwise healthy individuals and the resulting economic importance has made rhinovirus infection the subject of extensive investigation.

The ability of chemical compounds to suppress the growth of viruses in vitro may be readily demonstrated using a virus plaque suppression test or a cytopathic effect test (CPE). Cf Siminoff, Applied Microbiology, 9(1), 66 (1961). Although a number of chemical compounds that inhibit picornaviruses have been identified, many are unacceptable due to 1) limited spectrum of activity, 2) undesirable side effects or 3) inability to prevent infection or illness in animals or humans. See Textbook of Human Virology, edited by Robert B. Belshe, chapter 16, "Rhinoviruses," Roland A. Levandowski, 391–405 (1985). Thus, despite the recognized therapeutic potential associated with a rhinovirus inhibitor and the research efforts expended thus far, a viable therapeutic agent has not yet emerged. For example, antiviral benzimidazole compounds have been disclosed in U.S. Pat. Nos. 4,008,243, 4,018,790, 4,118,573, 4,118,742 and 4,174,454.

Accordingly, the present invention provides novel pyridoimidazole compounds which inhibit the growth of picornaviruses, such as rhinoviruses (bovine and human) and the like, enteroviruses such as polioviruses and the like, coxsackieviruses of the A and B groups, or echo virus, cardioviruses such as encephalomyocarditis virus (EMC) and the like, apthoviruses such as foot and mouth disease virus and the like, and Hepatitis viruses such as Hepatitis C virus and the like.

SUMMARY OF THE INVENTION

The present invention provides compounds of Formula (I):

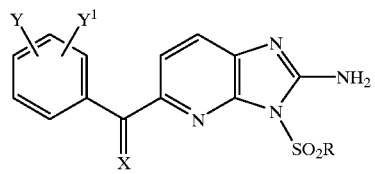

wherein:
R is $C_1$–$C_6$ alkyl, phenyl, or substituted phenyl;
Y and $Y^1$ are independently hydrogen, halo, or trifluoromethyl;
X is N—OH, O, or $CHR^1$;
$R^1$ is hydrogen, halo, CN, $C_1$–$C_4$ alkyl, —C≡CH, $CONR^2R^3$, $COR^2$, or $CO_2R^2$; and
$R^2$ and $R^3$ are independently hydrogen or $C_1$–$C_4$ alkyl;
or pharmaceutically acceptable salts thereof.

The present invention also provides pharmaceutical formulations comprising a compound of the present invention, or a pharmaceutically acceptable salt thereof, in combination with a pharmaceutically acceptable carrier, diluent or excipient thereof.

The present invention also provides a method for inhibiting a picornavirus comprising administering to a host in need thereof, an effective amount of a compound of Formula I, or a pharmaceutically acceptable salt thereof.

The present invention also provides a method for inhibiting a Hepatitis C virus comprising administering to a host in need thereof, an effective amount of a compound of Formula I, or a pharmaceutically acceptable salt thereof.

The present invention also provides for the use of compounds of Formula (I) in inhibiting a picornavirus, a rhinovirus, or a Hepatitis virus.

DETAILED DESCRIPTION OF THE INVENTION

The present invention relates to pyridoimidazole compounds of Formula (I), as described above, that are useful as antiviral agents.

All temperatures stated herein are in degrees Celsius (° C.). All units of measurement employed herein are in weight units except for liquids which are in volume units.

As used herein, the term "$C_1$–$C_6$ alkyl" represents a straight or branched alkyl chain having from one to six carbon atoms. Typical $C_1$–$C_6$ alkyl groups include methyl, ethyl, propyl, isopropyl, butyl, isobutyl, sec-butyl, t-butyl, pentyl, neo-pentyl, hexyl and the like. The term "$C_1$–$C_6$ alkyl" includes within its definition the term "$C_1$–$C_4$ alkyl."

"Halo" represents chloro, fluoro, bromo or iodo.

"Substituted phenyl" represents a phenyl ring substituted with halo, $C_1$–$C_4$ alkyl, or trifluoromethyl.

As mentioned above, the invention includes the pharmaceutically acceptable salts of the compounds defined by Formula (I). Although generally neutral, a compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are, but are not intended to be limited to, inorganic acids such as: hydrochloric acid, hydrobromic acid, hydroiodic acid, sulfuric acid, phosphoric acid, and the like, and organic acids such as: p-toluenesulfonic acid, methanesulfonic acid, oxalic acid, p-bromophenylsulfonic acid, carbonic acid, succinic acid, citric acid, benzoic acid, acetic acid, and the like.

Examples of such pharmaceutically acceptable salts are, but are not intended to be limited to, the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napthalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

The pharmaceutically acceptable salts of the invention are typically formed by reacting a compound of Formula (I) with an equimolar or excess amount of acid or base. The reactants are generally combined in a neutral solvent such as diethyl ether or benzene, for acid addition salts, or water or alcohols for base addition salts. The salts normally precipitate out of solution within about one hour to about ten days and can be isolated by filtration or other conventional methods.

The claimed compounds can occur in either the cis or trans configuration. For the purposes of the present application, cis refers to those compounds where the substituent on the alkene moiety is cis to the phenyl ring and trans refers to those compounds where the substituent on the alkene moiety is trans to the phenyl ring. Both isomers and mixtures thereof are included within the scope of the present invention.

The following lettered paragraphs represent embodiments of the present invention that are preferred. Preferred compounds of Formula (I) are those wherein:

(a) Y and $Y^1$ are independently halo, hydrogen, or trifluoromethyl;

(b) Y and $Y^1$ are independently halo or hydrogen;

(c) Y and $Y^1$ are independently hydrogen or fluoro;

(d) Y and $Y^1$ are both fluoro;

(e) X is NOH or $CHR^1$;

(f) X is $CHR^1$;

(g) R is phenyl or $C_1$–$C_6$ alkyl;

(h) R is isopropyl (i) $R^1$ is hydrogen, halo, CN, $CONR^2R^3$.

(j) $R^1$ is halo, hydrogen, or $CONR_2R_3$;

(k) $R^1$ is CN, or $CONR_2R_3$.

Especially preferred compounds of Formula (I) are those wherein:

(l) X is $CHR^1$; $R^1$ is $CONR_2R_3$; $R_2$ and $R_3$ are independently hydrogen, methyl, or ethyl; Y and $Y^1$ are independently fluoro or hydrogen; and R is isopropyl.

The compounds of Formula (I) can be prepared according to synthetic methods known in the art. The compounds of Formula (I) wherein X=O are intermediates to other compounds of Formula (I) and can be prepared according to the procedures shown in Scheme 1.

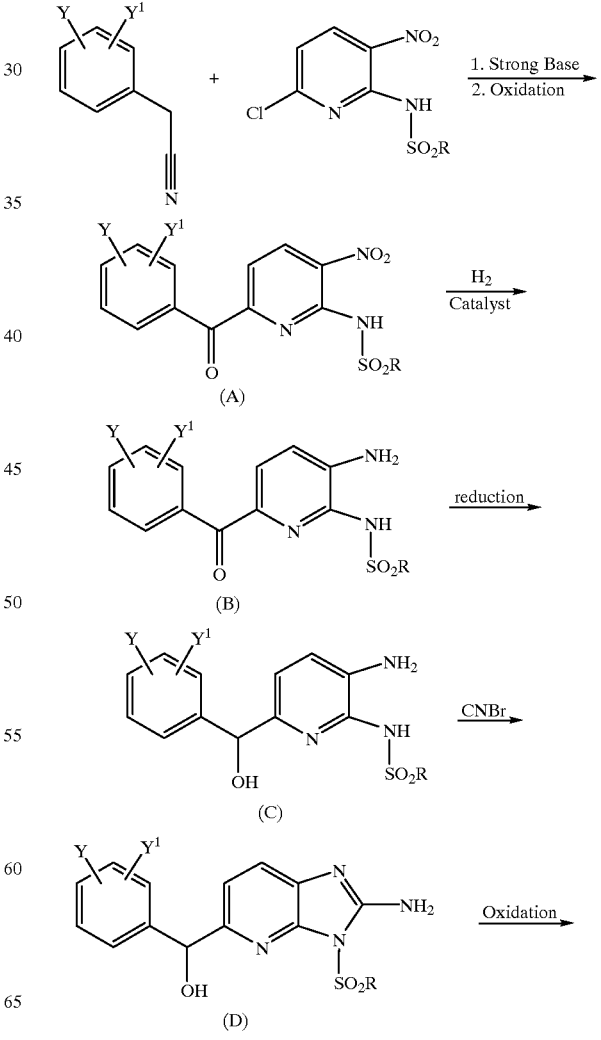

-continued

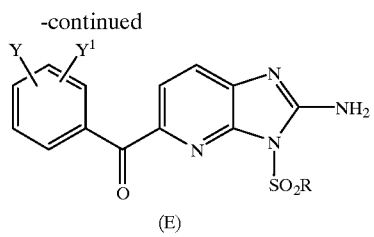

(E)

Y, Y¹, and R are as defined above.

Compounds of Formula (A) can be prepared by deprotonation of the corresponding phenylacetonitrile with a strong base in an aprotic solvent and addition of 2-chloro-5-nitro-6-alkylsulfonamylpyridine. The reaction is monitored by TLC and when substantially complete, an oxidizing agent is added to form the compounds of Formula (A). Suitable strong bases include, but are not limited to, alkyl lithiums, lithium diisopropylamine, lithium bistrimethylsilylamide, and the like. Potassium t-butoxide is the preferred base. Suitable solvents include, but are not limited to, diethyl ether, tetrahydrofuran, methylene chloride, chloroform, dimethylsulfoxide, and the like. Dimethylformamide is the preferred solvent. Suitable oxidizing agents include, but are not limited to, peroxyacids such as metachloroperbenzoic acid, sodium hypochlorite/acetic acid, molecular oxygen, chromium trioxide/acetic acid, and the like. Hydrogen peroxide is the preferred oxidizing agent. The phenylacetonitrile is generally employed in a substantial molar excess. For example, from about a 3 to 10 molar excess, relative to the 2-chloro-5-nitro-6-alkylsulfonylpyridine, is common. A 3.2 molar excess is typically preferred. The oxidizing agent is generally employed in a substantial molar excess. For example, from about a 3 to 10 molar excess, relative to the 2-chloro-5-nitro-6-alkylsulfonylpyridine, is common. A 6.1 molar excess is typically preferred. The reaction is preferably carried out at about 0° C. when adding the 2-chloro-5-nitro-6-alkylsulfonylpyridine, and then at 25° C. for 24 hours.

The compounds of Formula (B) can be prepared by selectively reducing compounds of Formula (A) according to procedures known in the art. For example, the nitro group contained in compounds of Formula (A) may be reduced by catalytic hydrogenation at low to moderate pressures. A suitable pressure range includes, but is not limited to, from about 14 to about 100 psi of hydrogen gas. The preferred pressure of hydrogen gas is 60 psi. Suitable catalysts include, but are not limited to, palladium on barium sulfate or palladium on carbon, and the like. Raney nickel is the preferred catalyst. Suitable solvents include, but are not limited to, toluene, ethanol, chloroform, methylene chloride, and the like. Tetrahydrofuran or ethyl acetate are the preferred solvents. The reaction is preferably carried out at about 25° C. for approximately 45 minutes.

The compounds of Formula (C) can be prepared by reduction of compounds of Formula (B) by procedures well known in the art. The transformation is carried out by dissolving or suspending the compounds of Formula (B) in an appropriate solvent then adding a reducing agent to afford the compounds of Formula (C). Suitable solvents include, but are not limited to, tetrahydrofuran, lower alcohols, ethyl acetate, methylene chloride, chloroform, and the like. Methanol is the preferred solvent. Suitable reducing agents include, but are not limited to, lithium aluminum hydride, triethylsilane/boron trifluoride, zinc/hydrochloric acid, lithium/ammonia/ammonium chloride, hydroiodic acid/phosphorous, and the like. Sodium borohydride is the preferred reducing agent. The reducing agent is generally employed in a substantial molar excess. For example, from about a 3 to about a 10 molar excess, relative to the compound of Formula (B), is common. A 4 molar excess is typically preferred. The reaction is preferably carried out at about 25° C. for approximately 3 hours.

The compounds of Formula (C) can be converted to compounds of Formula (D) by procedures known in the art. For example, the compounds of Formula (C) are dissolved in an appropriate solvent and cyanogen bromide added to furnish the compounds of Formula (D). Suitable solvents include, but are not limited to, lower alcohols, methylene chloride, ethyl acetate, tetrahydrofuran, chloroform, and the like. Acetonitrile and methanol are the preferred solvent. The cyanogen bromide is generally employed in a substantial molar excess. For example from about a 3 to about a 10 molar excess relative to the compound of Formula (C), is common. A 5 molar excess is generally preferred. The reaction is preferably carried out at about 25° C. for approximately 24 hours.

The compounds of Formula (E) can be prepared from compounds of Formula (D) by methods well known in the art. For example, compounds of Formula (D) are dissolved or suspended in an appropriate solvent and an appropriate oxidizing agent is added to yield compounds of Formula (E). Suitable solvents include, but are not limited to, methylene chloride, ethyl acetate, tetrahydrofuran, lower alcohols, chloroform, acetonitrile, and the like. Acetone is the preferred solvent. Suitable oxidizing agents include, but are not limited to, hydrogen peroxide, peroxyacids such as metachloroperbenzoic acid, sodium hypochlorite/acetic acid, chromium trioxide/acetic acid, and the like. Manganese dioxide is the preferred oxidizing agent. The oxidizing agent is generally employed in a substantial molar excess. For example from about a 3 to about a 40 molar excess, relative to the compound of Formula (D), is common. A 25 molar excess is generally preferred. The reaction is preferably carried out at about 56° C. for approximately 48 hours.

The compounds of Formula (I) where X=CH, and Z=CONH$_2$, COR$^2$, or CO$_2$R$^2$, are prepared according to the procedures shown in Scheme 2.

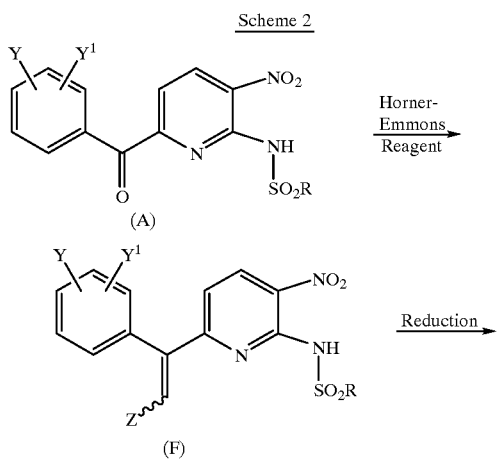

Scheme 2

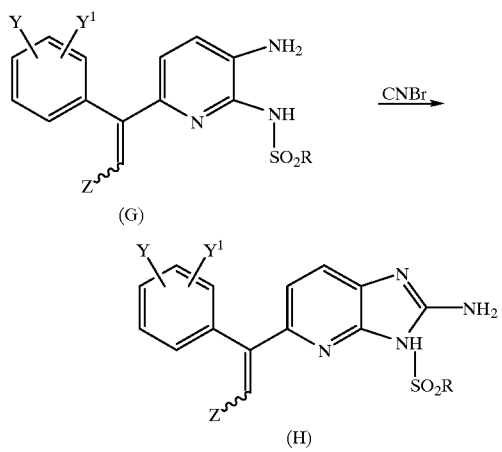

(G)

(H)

where Y, Y¹, Z, and R are defined as above.

The compounds of Formula (F) can be provided by methods well known in the art. For example, an appropriately substituted Horner-Emmons reagent (see *Organic Reactions,* 1977 Volume 25, pg. 73.) is deprotonated with a strong base in an aprotic solvent and a compound of Formula (A) added to afford compounds of Formula (F). Suitable strong bases include, but are not limited to, alkyl lithiums, lithium diisopropylamine, lithium bistrimethylsilylamide, and the like. Potassium t-butoxide is the preferred base. Suitable solvents include, but are not limited to, diethyl ether, tetrahydrofuran, methylene chloride, chloroform, dimethylsulfoxide, and the like. Dimethylformamide and tetrahydrofuran are the preferred solvent. The Horner-Emmons reagent is generally employed in a slight molar excess. For example, from about a 1 to 2 molar excess, relative to the 2-alkylsulfonamyl-3-nitro-6-benzoylpyridine (A), is common. A 1.1 molar excess is typically preferred. The reaction is preferably carried out at about 0° C. when adding the compound of Formula (A), and then at about 25° C. for approximately 1 hour.

Compounds of Formula (G) can be prepared by selective reduction of compounds of Formula (F) by procedures well known in the art. For example, the transformation is carried out by dissolving or suspending the compounds of Formula (F) in an appropriate solvent then adding a reducing agent to afford the compound of Formula (G). Suitable solvents include, but are not limited to, lower alcohols, ethyl acetate, methylene chloride, chloroform, and the like. Methanol, tetrahydrofuran, and water are the preferred solvents. Suitable reducing agents include, but are not limited to, lithium aluminum hydride, triethylsilane/boron trifluoride, zinc/hydrochloric acid, lithium/ammonia/ammonium chloride, hydroiodic acid/phosphorous, and the like. Sodium hydrosulfite/sodium bicarbonate is the preferred reducing agent. The reducing agent is generally employed in a substantial molar excess. For example, from about a 3 to 10 molar excess, relative to the compound of Formula (F), is common. A 4 to 8 molar excess of hydrosulfite and bicarbonate respectively is typically preferred. The reaction is preferably carried out at about 25° C. for approximately 1 hour.

The compounds of Formula (H) can be prepared from compounds of Formula (G) in a manner substantially analogous to the conversion of compounds of Formula (C) to compounds of Formula (D) described in Scheme 1 to give compounds of Formula (H).

The compounds of Formula (I) where X=NOH, or CH—Z, and Z=H, CN, or CONR²R³ can be prepared from compounds of Formula (E) according to the procedures shown in Scheme 3.

Scheme 3

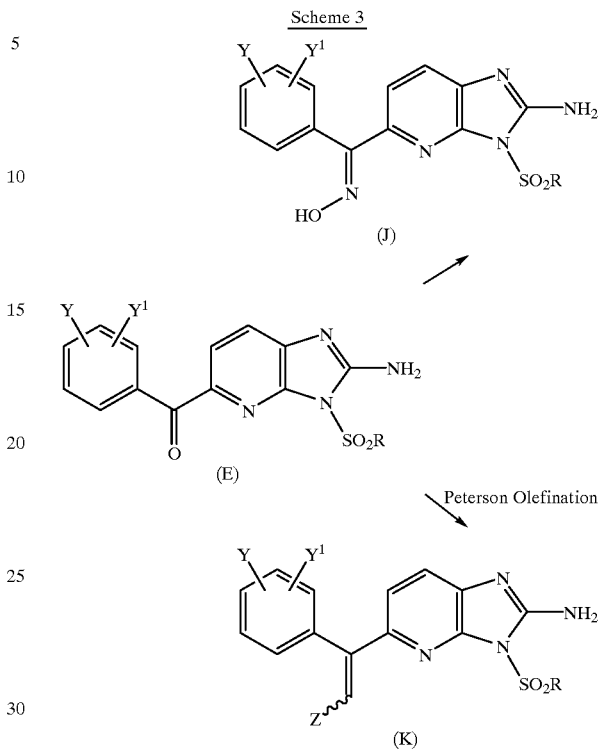

(J)

(E)

Peterson Olefination (K)

where Y, Y¹, Z, and R are as defined above.

The compounds of Formula (J) can be prepared from compounds of Formula (E) by well known methods in the art. For example, compounds of Formula (E) can be dissolved or suspended in an appropriate solvent and hydroxylamine is added to afford the compounds of Formula (J). Suitable solvents include, but are not limited to, lower alcohols, ethyl acetate, methylene chloride, chloroform, and the like. Methanol or pyridine is the preferred solvent. The hydroxylamine is generally employed in a substantial molar excess. For example, from about a 3 to 10 molar excess, relative to the compound of Formula (E), is common. A 5.0 molar excess is typically preferred. The reaction is preferably carried out at about 25° C. for approximately 24 hours.

The compounds of Formula (K) can be prepared from compounds of Formula (E) by well known methods in the art. For example, an appropriately substituted Peterson Olefination Reagent (see Organic Reactions, 1990, volume 38, pg. 1.) can be dissolved in a suitable solvent and deprotonated with a strong base. A compound of Formula (E) is then added to afford the compounds of Formula (K). Suitable strong bases include, but are not limited to, potassium t-butoxide, alkyl lithiums, lithium diisopropylamine, lithium bistrimethylsilylamide, and the like. n-Butyl lithium is the preferred base. Suitable solvents include, but are not limited to, diethyl ether, methylene chloride, chloroform, dimethylformamide, dimethylsulfoxide, and the like. Tetrahydrofuran is the preferred solvent. The Peterson Reagent is generally employed in a substantial molar excess. For example, from about a 3 to 10 molar excess, relative to the compound of Formula (E), is common. A 5.0 molar excess is typically preferred. The reaction is preferably carried out at about −78° C. when deprotonating the Peterson Reagent and when adding the compound of Formula (E), and then at about 25° C. for approximately 24 hours.

The compounds of Formula (L) where X=CHZ and Z=Halo can be prepared from compounds of Formula (K), where Z=H, according to the procedure shown in Scheme 4.

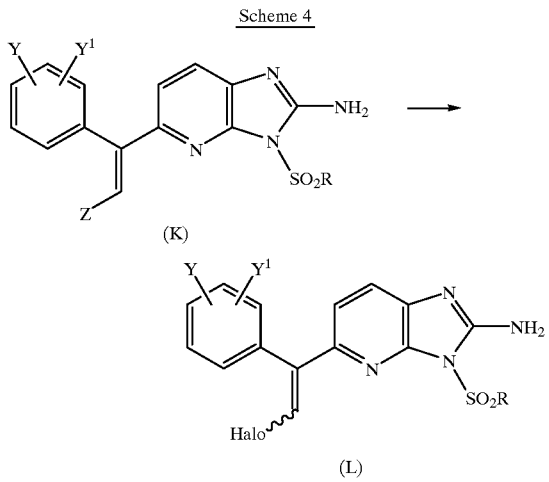

Scheme 4 where Z, Y, Y¹, Halo, and R are as defined above.

Compounds of Formula (L) can be prepared from compounds of Formula (K) where Z=H by well known methods in the art. For example, a compound of Formula (L) can be dissolved in a suitable solvent and an appropriate halogenating agent added to form the compound of Formula (L). Suitable solvents include, but are not limited to, methylene chloride, tetrahydrofuran, chloroform, acetonitrile, acetic acid, and the like. Tetrahydrofuran and carbon tetrachloride are the preferred solvents. Suitable halogenating agents include, but are not limited to, benzeneseleninylchloride/ aluminum chloride, thionyl chloride, molecular bromine, $CsSO_4F$, NFTh, and the like. The halogenating reagent is generally employed in a slight molar excess. For example, from about a 1 to 2 molar excess, relative to a compound of Formula (K), is common. A 1.1 molar excess is typically preferred. The reaction is preferably carried out at about −10° C. when adding the halogenating agent and then at about 22° C. for approximately 1 hour.

Compounds of Formula (I) where X=CH and Z=$C_1$–$C_5$ alkyl can be prepared by well known methods in the art. For example, compounds of Formula (H) (where Z=$COR^1$ and $R^1$=C1–C4 alkyl) can be dissolved in a suitable solvent and a reducing agent added to afford compounds of Formula (M). Suitable solvents include, but are not limited to, lower alcohols, chloroform, methylene chloride, tetrahydrofuran, dimethylformamide, dimethylsulfoxide, ethyl acetate, toluene, 1,2-dichloroethane, and the like. Suitable reducing agents include but are not limited to lithium aluminum hydride/$AlCl_3$, hydroiodic acid/phosphorous, sodium borohydride/$AlCl_3$, and the like. (For example, see A. Srikrishna, R. Viswajanani, J. A. Sattigeri, and C. V. Yelamaggad, *Chemoselective Reduction Deoxygenation of α,β Unsaturated Ketones and Allyl Alcohols*, Tetrahedron Letters, 36(13)2347–50 (1995))

In general, the reactions of Schemes 1–4 are substantially complete in about 15 minutes to 72 hours when conducted at a temperature range of from about −78° C. to the reflux temperature of the reaction mixture. A skilled artisan would appreciate that the rate of a reaction generally increases with an increase in temperature. It is often advantageous, however, to conduct reactions at a slower rate to better control the number and quantity of side products generated. The choice of reaction solvent is not critical so long as the solvent employed is inert to the ongoing reaction and the reactants are sufficiently solubilized to effect the desired reaction. Once a reaction is complete, the intermediate compound may be isolated, if desired, by procedures known in the art. For example, the compound may be crystallized and then collected by filtration, or the reaction solvent may be removed by extraction, evaporation, or decantation. The intermediate may be further purified, if desired by common techniques such as recrystallization or chromatography over solid supports such its silica gel or alumina. The compounds of Formula A–L are preferably isolated before use in subsequent reactions.

A skilled artisan would appreciate that the ratio of cis/ trans products isolated by the schemes disclosed herein can vary widely, from almost completely cis or trans to equally proportions of both, depending upon the starting materials employed and the reaction conditions utilized.

PREPARATIONS AND EXAMPLES

The following Preparations and Examples further illustrate specific aspects of the present invention. It is to be understood, however, that these examples are included for illustrative purposes only and are not intended to limit the scope of the invention in any respect and should not be so construed.

In the following Preparations and Examples, the terms melting point, nuclear magnetic resonance spectra, electron impact mass spectra, field desorption mass spectra, fast atom bombardment mass spectra, infrared spectra, ultraviolet spectra, elemental analysis, high performance liquid chromatography, and thin layer chromatography are abbreviated "m.p.", "NMR", "EIMS", "MS(FD)", "MS(FAB)", "IR", "UV", "Analysis", "HPLC", and "TLC", respectively. The values reported for MS(FD) correspond to mass numbers unless otherwise indicated. In addition, the absorption maxima listed for the IR spectra are only those of interest and not all of the maxima observed.

The NMR spectra were obtained on a Brüker Corp. 270 MHz instrument or on a General Electric QE-300 300 MHz instrument. The chemical shifts are expressed in delta (δ) values (parts per million downfield from tetramethyl-silane). The MS(FD) spectra were taken on a Varian-MAT 731 Spectrometer using carbon dendrite emitters. EIMS spectra were obtained on a CEC 21-110 instrument from Consolidated Electrodynamics Corporation. IR spectra were obtained on a Perkin-Elmer 281 instrument. UV spectra were obtained on a Cary 118 instrument. TLC was carried out on E. Merck silica gel plates. Melting points are uncorrected.

The cis and trans forms of the compounds of the present invention can be separated using column chromatography, for example reverse phase HPLC. The compounds may be eluted from the column using an appropriate ratio of acetonitrile and water or methanol and water.

The compounds employed as initial starting materials in the synthesis of the compounds of this invention are known in the art, and, to the extent not commercially available are readily synthesized by standard procedures commonly employed in the art.

It will be understood by those skilled in the art that in performing the processes described above it may be desirable to introduce chemical protecting groups into the reactants in order to prevent secondary reactions from taking place. For example, any amine, alcohol, alkylamine or carboxy groups which may be present on the reactants may be protected using any standard amino- or carboxy-protecting group which does not adversely affect the remainder of the molecule's ability to react in the manner desired. The various protective groups may then be removed simultaneously or successively using methods known in the art.

In conjunction with the NMR spectra, the following abbreviations are used: "s" is singlet, "d" is doublet, "dd" is doublet of doublets, "t" is triplet, "q" is quartet, "m" is multiplet, "dm" is a doublet of multiplets and "br.s", "br.d", "br.t", and "br.m" are broad singlet, doublet, triplet, and multiplet respectively. "J" indicates the coupling constant in Hertz (Hz). Unless otherwise noted, NMR data refers to the free base of the subject compound.

When used within the preparations, the terms "MS", "Analysis", "IR", "UV", and "NMR" indicate that the corresponding mass spectrum, elemental analysis, infrared spectrum, ultraviolet spectrum, and nuclear magnetic resonance spectrum were consistent with the desired product.

Preparation 1

Isopropylsulfonamide

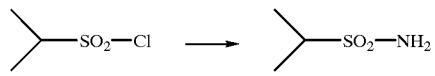

A flask was fitted with a cold finger condenser, a septum, and a tygon tube open to the atmosphere. An atmosphere of $N_2$ was placed in the flask while cooling it to −78° C. Ammonia (g) was condensed into the flask to an approximate volume of 150 ml. The flask was then charged with 300 ml of cold tetrahydrofuran (−78° C.). The solution was magnetically stirred as isopropylsulfonylchloride was added over 20 minutes. After the addition was complete, the flask was allowed to warm to room temperature overnight. By the next day, a white precipitate had formed and was filtered off and washed with 1200 ml of ethyl acetate. The filtrate was concentrated in vacuo to give 109 g of product. (100%). MS(FD), IR, Analysis, UV, NMR.

Preparation 2

2-Chloro-5-nitro-6-isopropylsulfonamylpyridine

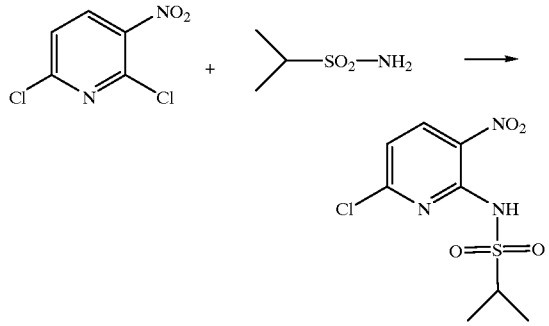

2,6-dichloro-5-nitropyridine (65.88, 313.1 mmol) and isopropylsulfonamide (46.17 g, 374.8 mmol) were dissolved in 700 ml of dry dimethylformamide. Lithium hydride (6.377 g, 803.1 mmol) was added in 1 portion creating an exotherm. After the solution cooled down (about 2 hours), 1100 ml of water was added and the mixture was acidified just slightly with 5N hydrochloric acid (pH between 6 and 7). The light yellow precipitate was filtered and washed with 2 L of $H_2O$ and 300 ml of ethyl acetate. The filter cake was placed in a vacuum oven at 55° C. overnight to dry. Yield was 53.9 g of product. (61.5%). MS(FD), Analysis, IR, UV, NMR.

Preparation 3

2-Isopropylsulfonamyl-3-nitro-6-benzoylpyridine

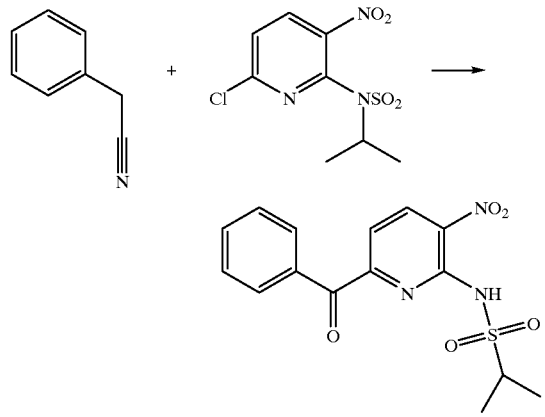

Phenylacetonitrile (7.54 g, 64.3 mmol) was dissolved in 60 ml of dimethylformamide and cooled to 0° C. with an ice bath. Potassium t-butoxide (7.22 g, 64.4 mmol) was added in one portion. In a separate flask, the 2-chloro-5-nitro-6-isopropylsulfonamylpyridine (5.54 g, 19.8 mmol) was dissolved with gentle heating in 60 ml of dimethylformamide and cannulated into the flask containing the phenylacetonitrile anion. The resulting solution was stirred for 3.5 hours at 0° C., then an additional hour at room temperature. An additional 0.555 g (4.95 mmol) of base was added, and after stirring for 0.5 hours, hydrogen peroxide (4.03 g, 118.8 mmol) was added. The reaction was allowed to stir for 24 hours and then the reaction was diluted to 450 ml with water. The product was precipitated by acidifying the solution to pH 2–3 with 5N hydrochloric acid. The mixture was chilled to 0° C. before filtering. The filter cake was rinsed with 50 ml of 0.2N hydrochloric acid and dried in a vacuum oven to yield 5.83 g of product. (84%). MS(FD), Analysis, IR, NMR.

Preparation 4

2-Isopropylsulfonamyl-3-nitro-6-(2,5-difluoro)benzoylpyridine

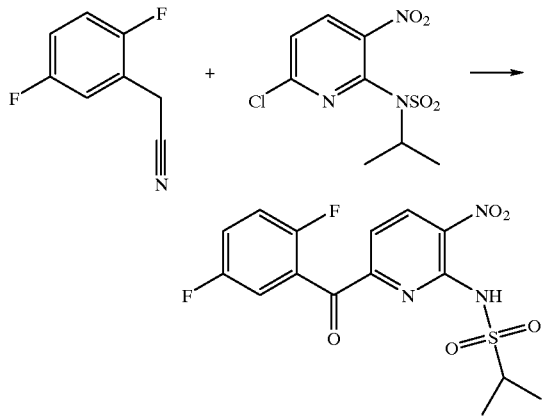

The 2,5-difluorophenylacetonitrile (109 g, 0.714 mmol) was coupled to 2-chloro-5-nitro-6-isopropylsulfonamylpyridine

Preparation 5

2-Isopropylsulfonamyl-3-nitro-6-(3-fluorobenzoyl)pyridine

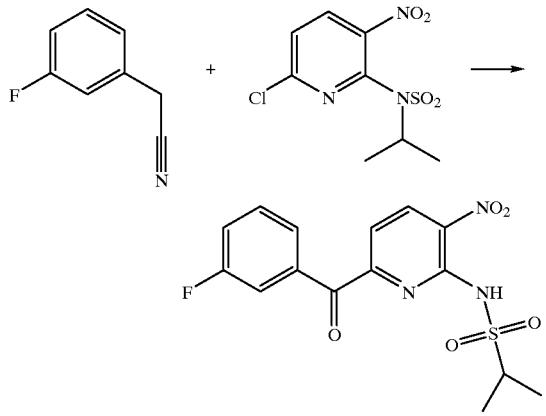

The 3-fluorophenylacetonitrile (48.31 g, 357.5 mmol) was coupled to the 2-chloro-5-nitro-6-isopropylsulfonamylpyridine in a manner substantially analogous to Preparation 3 to give 35.26 g of 3-fluorophenylnitropyrido ketone. (87%). MS(FD), IR, NMR.

Preparation 6

2-Isopropylsulfonamyl-3-amino-6-(2,5-difluoro)benzoylpyridine

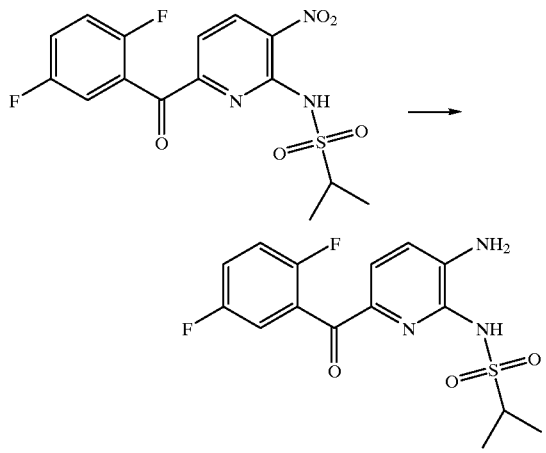

The 2-isopropylsulfonamyl-3-nitro-6-(2,5-difluoro)benzoylpyridine (1.36 g, 3.54 mmol) was dissolved in 12.5 ml of ethyl acetate and 37.5 ml of tetrahydrofuran. Raney Nickel (40.0 mg) was added and the reaction mixture was placed under an atmosphere of $H_2(g)$ at 60 psi at 25° C. for 0.75 hours. The reaction was filtered through celite then concentrated in vacuo. The crude product was dissolved in methylenechloride and purified by normal phase flash chromatography to give 0.800 g of product. (63.9%). MS(FD), Analysis, NMR.

Preparation 7

2-Isopropylsulfonamyl-3-amino-6-benzoylpyridine

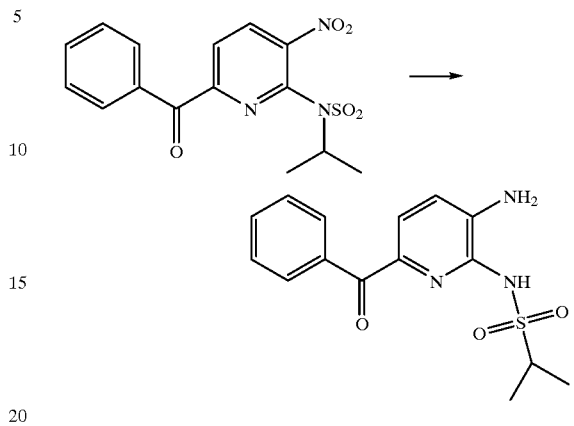

The 2-isopropylsulfonamyl-3-nitro-6-benzoylpyridine (2.43 g, 6.96 mmol) was selectively hydrogenated in a manner substantially analogous to Preparation 6 to give 0.700 g of product. (31%). MS(FD), Analysis, IR, NMR.

Preparation 8

2-Isopropylsulfonamyl-3-amino-6-(2,5-difluoro)phenylcarbinolpyridine

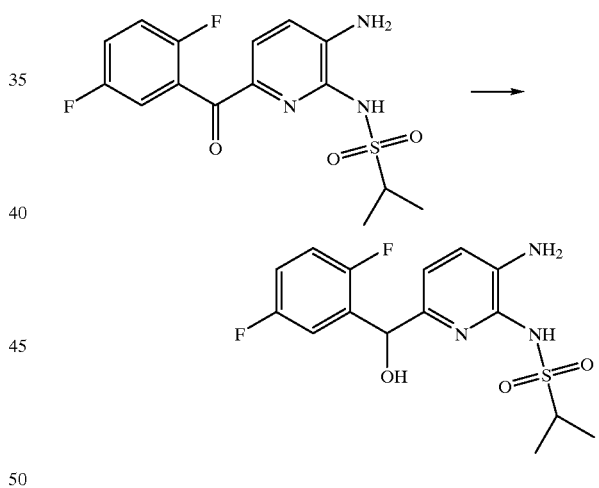

The 2-isopropylsulfonamyl-3-amino-6-(2,5-difluoro)benzoylpyridine (15.8 g, 44.5 mmol) was suspended in 275 ml of methanol and the sodium borohydride was added in 3 portions. The mixture was allowed to stir for 3 hours under $N_2$. The reaction was checked by TLC and when complete the reaction was concentrated in vacuo, the residue redissolved in 250 ml of methanol, then re-concentrated in vacuo. The residue was then dissolved in 250 ml of ethyl acetate and washed with 40 ml each of 1N hydrochloric acid and brine. The mother liquor was then dried over magnesium sulfate, filtered, then concentrated in vacuo. The residue was triturated with 50 ml of ethyl acetate and the solids filtered. The filter cake was washed with 10 ml of ethyl acetate. The filter cake was dried in a vacuum oven at 50° C. overnight to give 13.1 g of product. (82.2%). MS(FD), Analysis, IR, UV, NMR.

in a manner substantially analogous to Preparation 3 to give 134.4 g of product. (101.4%). HPLC.

Preparation 9

2-Isopropylsulfonamyl-3-amino-6-phenylcarbinolpyridine

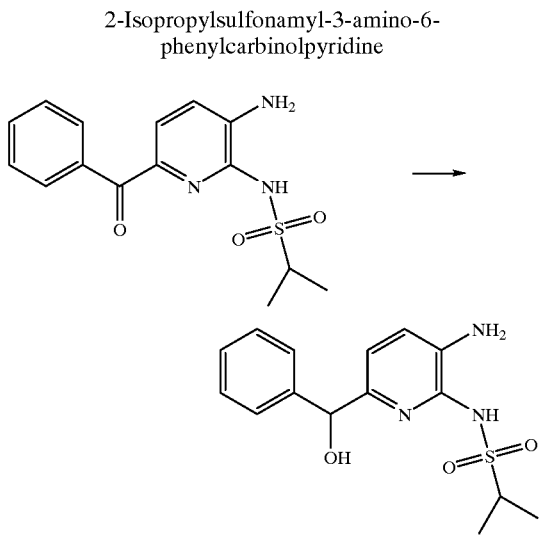

The 2-isopropylsulfonamyl-3-amino-6-benzoylpyridine (2.55 g, 8.00 mmol) was reduced in a manner substantially analogous to Preparation 8 to give 2.7 g of product. (100%) MS(FD), IR, NMR.

Preparation 10

2-Isopropylsulfonamyl-3-amino-6-(3-fluoro)phenylcarbinolpyridine

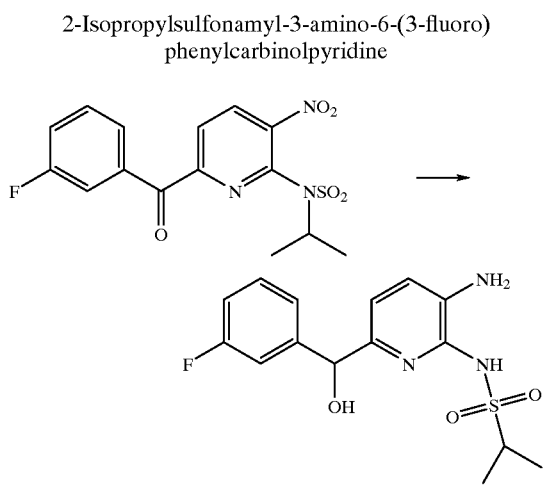

The 2-isopropylsulfonamyl-3-nitro-6-(3-fluoro)benzoylpyridine (34.2 g, 93.1 mmol) was reduced in a manner substantially analogous to the combination of Preparations 6 and 9, without isolating the intermediate from Preparation 6, to yield 21.1 g of product. (66.6%). MS(FD), IR, NMR.

Preparation 11

1-Isopropylsulfonamyl-2-amino-6-(2,5-difluoro)phenylcarbinol-7-pyridoimidazole

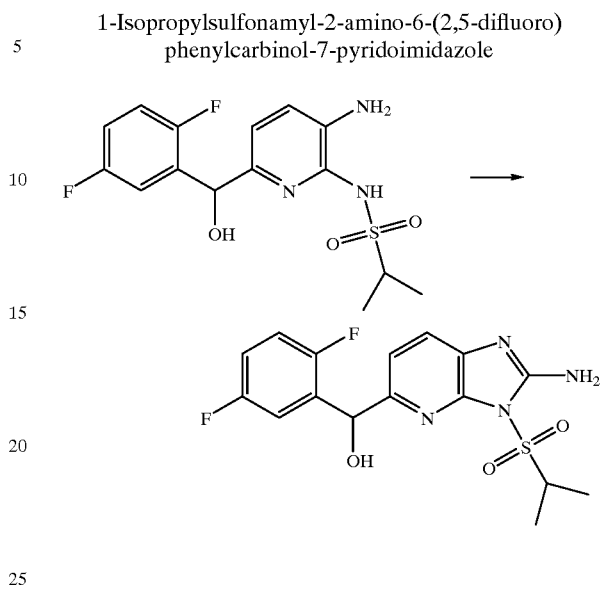

The 2-isopropylsulfonamyl-3-amino-6-(2,5-difluoro)phenylcarbinolpyridine (13.06 g, 36.58 mmol) was suspended in 125 ml of methanol and 12 ml of water. Cyanogen bromide (36.58 ml, 182.9 mmol) was added and the suspension turned to a solution within 5 minutes. The reaction was allowed to stir overnight before concentrating in vacuo. The residue was triturated with ethyl acetate. The solids were filtered and washed with 150 ml of ethyl acetate. The filter cake was dried in a vacuum oven at 50° C. to give 12.6 g of product. (90.0%). MS(FD), IR, UV, NMR.

Preparation 12

1-Isopropylsulfonamyl-2-amino-6-phenylcarbinol-7-pyridoimidazole

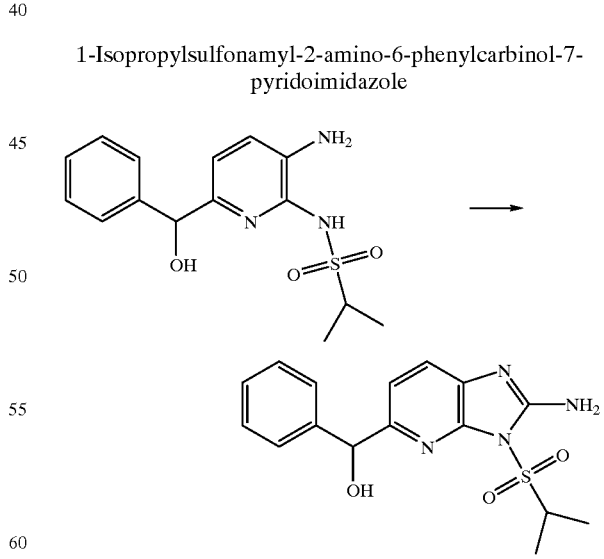

The 2-isopropylsulfonamyl-3-amino-6-phenylcarbinolpyridine (25.25 g, 78.80 mmol) was converted to the product in a manner substantially analogous to Preparation 11 to yield 4.95 g. (18%). MS(FD), NMR.

Preparation 13

1-Isopropylsulfonamyl-2-amino-6-(3-fluoro)phenylcarbinol-7-pyridoimidazole

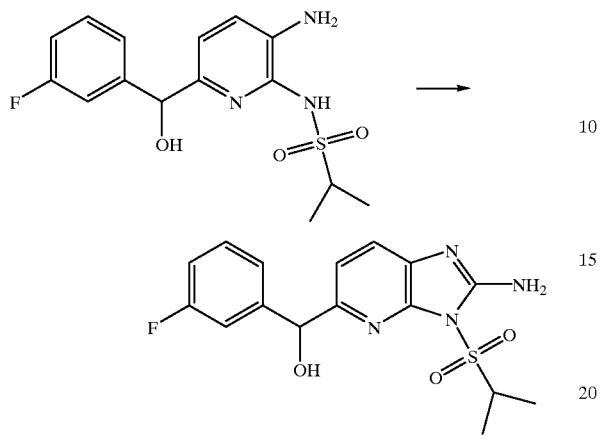

The 2-isopropylsulfonamyl-3-amino-6-(3-fluoro)phenylcarbinolpyridine (21.06 g, 62.00 mmol) was converted to product in a manner substantially analogous to Preparation 11 to yield 17.05 g. (75%). IR, NMR.

Preparation 14

Bis-N,α-trimethylsilylacetamide

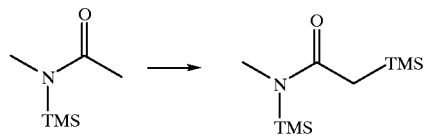

An oven dried flask was charged with N-trimethylsilylacetamide (16.0 ml, 99.8 mmol) and 150 ml of anhydrous tetrahydrofuran. The solution was cooled to −78° C. and n-butyl lithium was added slowly keeping the temperature of the reaction below −70° C. After the addition was complete, the mixture was allowed to stir for 1.5 hours at −78° C. Chlorotrimethylsilane (12.8 ml, 100.9 mmol) was added and the solution was allowed to warm to 25° C. over 18 hours. The tetrahydrofuran was removed in vacuo and the precipitate (lithium chloride) was filtered and washed with 5 ml of tetrahydrofuran. The filtrate was concentrated in vacuo and the residue was fractionally distilled under high vacuum to give 5.75 g of the Peterson Reagent. (26.5%). NMR.

Preparation 15

Diethylphosphonacetamide

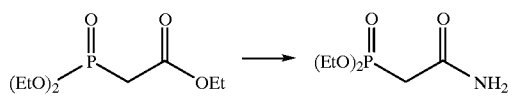

The triethylphosphonacetate (22.4 g, 100 mmol) was dissolved in 150 ml of methanol and chilled to 0° C. Ammonia (g) was bubbled through the solution for 15 minutes. When the addition was complete, the reaction was allowed to warm to 25° C. and stir for 72 hours. The methanol was removed in vacuo to yield 19.5 g of product. (100%) NMR.

Preparation 16

2-Isopropylsulfonamyl-3-nitro-6-(1-phenyl-2-trans-carboxamyl)ethylenylpyridine

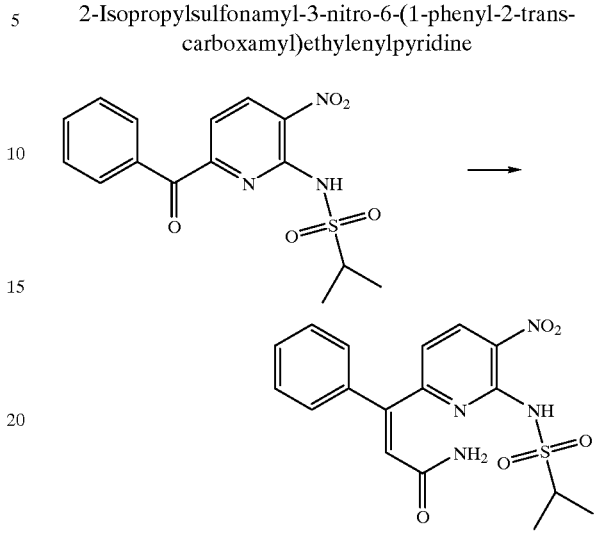

The diethylphosphonacetamide, from preparation 15, (6.99 g, 22.0 mmol) was dissolved in 50 ml of tetrahydrofuran and cooled to 0° C. and potassium t-butoxide (4.94 g, 44.0 mmol) was added. The solution was cooled to −78° C. and the 2-isopropylsulfonamyl-3-nitro-6-benzoylpyridine (6.99 g, 20.0 mmol), dissolved/suspended in 75 ml tetrahydrofuran, was added to the reaction at a rate sufficient to keep the temperature of the reaction below −70° C. After the addition was complete, the reaction was allowed to stir at −78° C. for 1 hour and then at 25° C. for 24 hours. The reaction was quenched and acidified with 5N hydrochloric acid. The mixture was partitioned between pH 7 buffer and ethyl acetate and the aqueous layer extracted twice with ethyl acetate. The combined organics were washed with brine, dried over magnesium sulfate, filtered, and concentrated in vacuo. The crude product was dissolved in 15:1:84 acetone:trifluoroacetic acid:methylenechloride and purified by normal phase chromatography to give 1.13 g of trans product. (14.4%). MS(FD), NMR.

Preparation 17

2-Isopropylsulfonamyl-3-amino-6-(1-phenyl-2-trans-carboxamyl)ethylenylpyridine

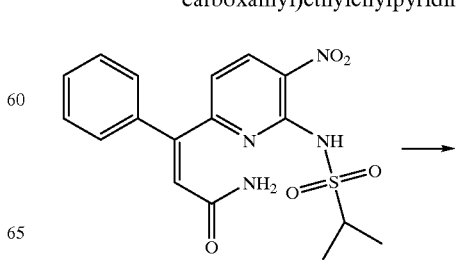

19

-continued

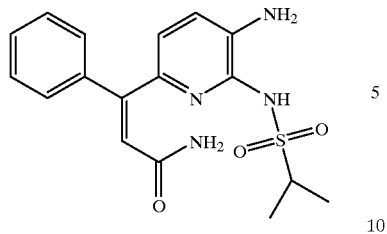

The 2-isopropylsulfonamyl-3-nitro-6-(1-phenyl-2-cis-carboxamyl)ethylenylpyridine (0.39 g, 1 mmol) was dissolved in 20 ml of methanol, 10 ml of tetrahydrofuran, and 10 ml of water. Sodium hydrosulfite (0.696 g, 4 mmol) was added followed by sodium bicarbonate (0.672 g, 8 mmol). The solution was allowed to stir for 0.5 hours and then the pH adjusted to 7 with 5N hydrochloric acid. The reaction was partitioned between ethyl acetate and water and the aqueous layer extracted 3 times with ethyl acetate. The combined organics were washed with brine, dried over magnesium sulfate, filtered, and concentrated in vacuo to give 130 mg of phenylaminopyrido vinylcarboxamide. HPLC

Example 1

1-Isopropylsulfonamyl-2-amino-6-(2,5-difluorobenzoyl)-7-pyridoimidazole

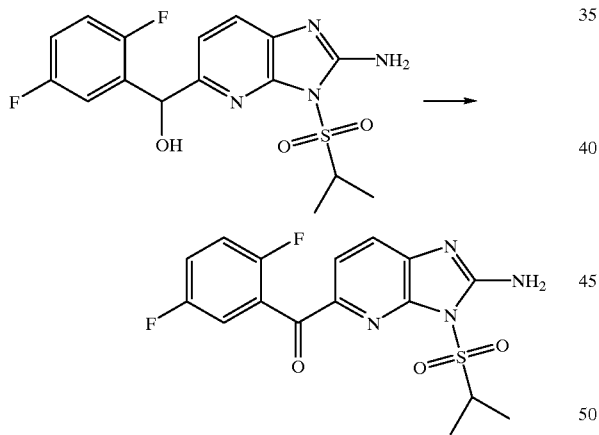

The 1-isopropylsulfonamyl-2-amino-6-(2,5-difluoro)phenylcarbinol-7-pyridoimidazole (12.6 g, 33.0 mmol) and manganese dioxide (67.5 g, 660 mmol) were suspended in 300 ml of acetone and heated to 55° C. for 24 hours. Additional manganese dioxide (14.35 g, 16.51 mmol) was added, and the reaction was heated to reflux for 24 hours and than allowed to stir at 25° C. for 48 hours. The mixture was filtered through celite and rinsed with 900 ml of tetrahydrofuran. The filtrate was concentrated in vacuo and the residue triturated with ethyl acetate and filtered to give 7.51 g of product. (60.0%). MS(FD) m/e 380. Anal Calcd for $C_{16}H_{14}F_2N_4O_3S$: C, 50.52; H, 3.71; N, 14.72. Found: C, 50.37; H, 3.80; N, 14.44.

20

Example 2

1-Isopropylsulfonamyl-2-amino-6-benzoyl-7-pyridoimidazole

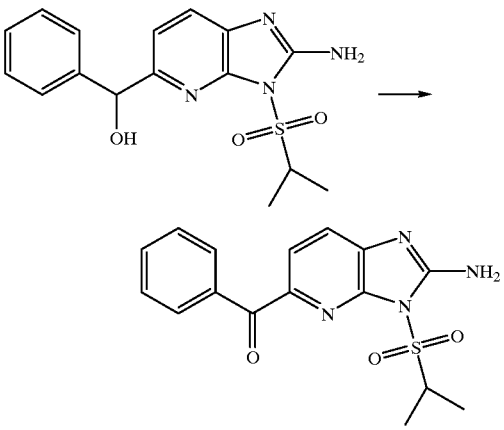

The 1-isopropylsulfonamyl-2-amino-6-phenylcarbinol-7-pyridoimidazole (4.95 g, 14.3 mmol) was dissolved/suspended in 150 ml of acetone. The mixture was stirred rapidly as manganese dioxide (37.3 g, 429 mmol) was added. The mixture was then heated to about 40° C. and stirred for 72 hours. TLC at that time indicated complete conversion to product. The mixture was allowed to cool before filtering it through celite. The filter cake celite was rinsed with acetone, acetonitrile, methanol, tetrahydrofuran, and finally acetone/methanol. The filtrate was concentrated in vacuo and the residue triturated with ethyl acetate/methanol. The triturated material was then dissolved in tetrahydrofuran and filtered. The filtrate was concentrated in vacuo to give 3.91 g of product. Anal Calcd for $C_{16}H_{16}N_4O_3S$: C, 55.80; H, 4.68; N, 16.27. Found: C, 55.53; H, 4.68; N, 16.17. IR—3394, 1636, 1591 cm$^{-1}$. UV $\lambda_{max}$, (e): 326 (19554), 246 (12960).

Example 3

1-Isopropylsulfonamyl-2-amino-6-(3-fluorobenzoyl)-7-pyridoimidazole

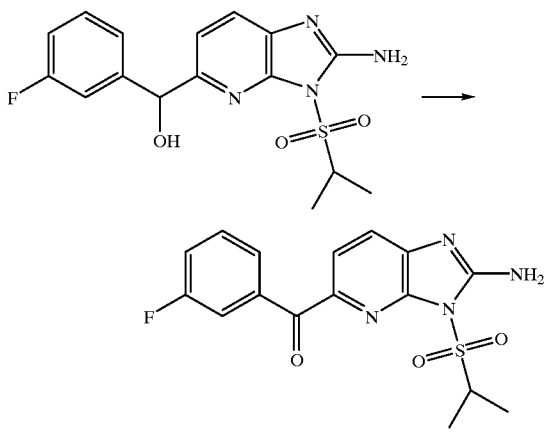

The 1-isopropylsulfonamyl-2-amino-6-(3-fluoro)phenylcarbinol-7-pyridoimidazole (16.39 g, 45.00 mmol) was suspended in 300 ml of acetone. The mixture was rapidly stirred as manganese dioxide (78.2 g, 900 mmol)

was added. The mixture was heated to about 40° C. and stirred for 24 hours. An additional 19.56 g (225.0 mmol) of manganese dioxide was added and the mixture was allowed to stir at 40° C. for 48 hours, and at 25° C. for 24 hours. TLC at that time indicated completion of the reaction. The mixture was filtered through celite and rinsed with (3×300 ml) tetrahydrofuran. The filtrate was concentrated in vacuo and the solid residue was triturated with ethyl acetate and filtered. The filtrate was concentrated in vacuo and the sold residue triturated with a smaller amount of ethyl acetate and filtered. The two filter cakes were combined for a total yield of 11.6 g of product. (71%). MS(FD) m/e 362.3. Anal Calcd for $C_{16}H_{15}FN_4O_3S$: C, 53.03; H, 4.17; N, 15.46. Found: C, 53.04; H, 4.19; N, 15.37.

Example 4

1-Isopropylsulfonamyl-2-amino-6-(1-[2,5-difluorophenyl]-2-trans-methylcarboxamylethylenyl)-7-pyridoimidazole

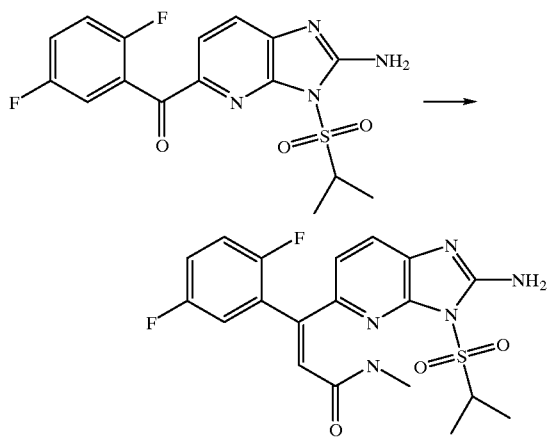

An oven dried flask was cooled under nitrogen and charged with 30 of anhydrous tetrahydrofuran and the Peterson Reagent (Preparation 14) (5.75 g, 26.4 mmol). The solution was cooled to −78° C. and the lithium bistrimethylsilylamide (1N in tetrahydrofuran, 26.4 ml, 26.4 mmol) was added slowly keeping the temperature of the reaction mixture below −60° C. Once the addition was complete, the mixture was allowed to stir for 2 hours at −78° C. The 1-isopropylsulfonamyl-2-amino-6-(2,5-difluorobenzoyl)-7-pyridoimidazole (2.01 g, 5.29 mmol), dissolved in 30 ml of anhydrous tetrahydrofuran, was added and the resulting solution was stirred at −78° C. for 4 hours and then allowed to warm to room temperature over 18 hours. The reaction was concentrated in vacuo then diluted to 22 ml with acetonitrile. The crude product was purified by reverse phase chromatography and then further purified by radial normal phase chromatography to give 0.180 g of a single trans isomer. MS(FD) m/e 435.1. Anal Calcd for $C_{19}H_{19}F_2N_5O_3S$: H, 4.40; N, 16.08. Found: H, 4.53; N, 16.16. IR—1639, 1611 cm$^{-1}$.

Example 5

1-Isopropylsulfonamyl-2-amino-6-cis-benzoxime-7-pyridoimidazole

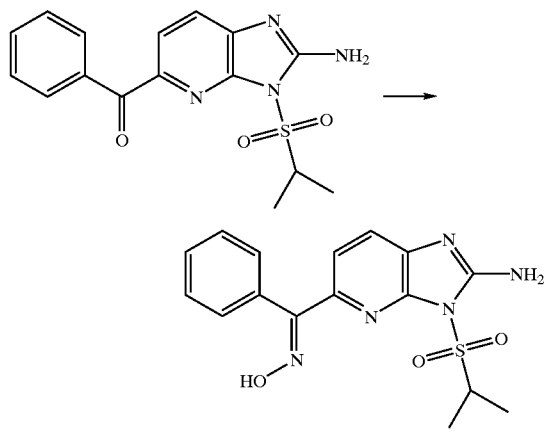

The 1-isopropylsulfonamyl-2-amino-6-benzoyl-7-pyridoimidazole (1.03 g, 3.00 mmol) was suspended in 12 ml of a 2:1 v:v mixture of methanol and pyridine. Hydroxylamine hydrochloride (1.03 g, 14.8 mmol) was added along with another 1.5 ml of pyridine and 10–15 ml of tetrahydrofuran to effect complete dissolution of the reactants. The solution was allowed to stir for 24 hours at 25° C. and then was concentrated in vacuo. The residue was partitioned between ethyl acetate and pH 7 buffer. The aqueous layer was separated and the pH adjusted to 6 with a saturated aqueous solution of sodium bicarbonate. The aqueous layer was then extracted with ethyl acetate and the organics combined and washed with brine, dried over magnesium sulfate, filtered, and concentrated in vacuo to give a yellow solid. The solid was triturated with ethyl acetate/ether and filtered. The filter cake was washed with methanol to yield 0.155 g of cis product. (14%). MS(FD) m/e 359.2, IR—3236, 3017, 2940, 1646, 1589 cm$^{-1}$.

Example 6

1-Isopropylsulfonamyl-2-amino-6-trans-benzoxime-7-pyridoimidazole

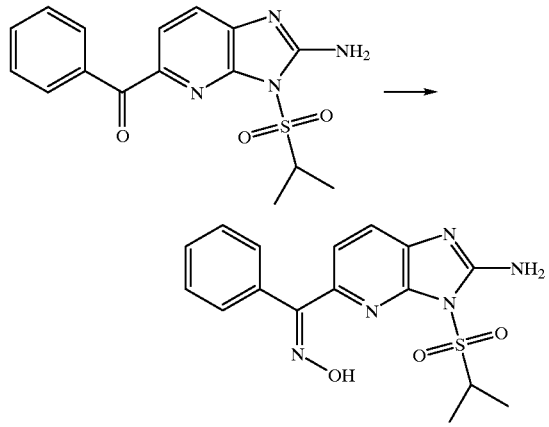

The 1-isopropylsulfonamyl-2-amino-6-benzoyl-7-pyridoimidazole (33 mg, 0.096 mmol) was suspended in methanol (1 ml) and 0.500 ml of pyridine. Additional pyridine was added until the ketone was in solution. Hydroxylamine hydrochloride was added in excess and the resulting solution was stirred at 40° C. for 2 hours. The solution was concentrated in vacuo and the residue triturated with water (15 ml). The water was pipetted away and the resulting solid was dried by azeotroping with methanol. The crude material was purified by reverse phase chromatography to give 20 mg of trans product. MS(FD) 359.1.

Example 7

1-Isopropylsulfonamyl-2-amino-6-(1-phenyl-2-methylcarboxamyl)ethylenyl-7-pyridoimidazole

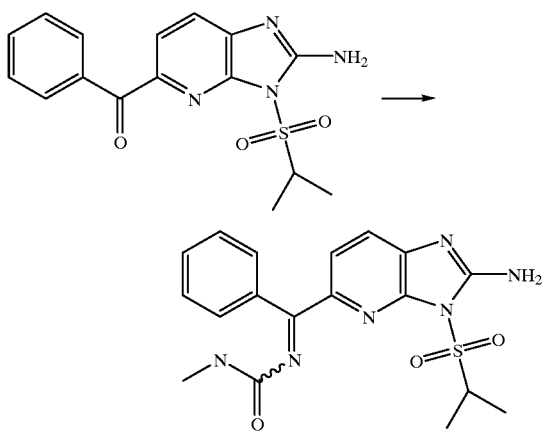

The Peterson Reagent (from Preparation 14) (1.08 g, 5.00 mmol) was dissolved in 15 ml of tetrahydrofuran and chilled to −78° C. The n-butyl lithium (1.6 M in hexanes, 2.5 ml, 4.0 mmol) was added via syringe so that the temperature of the reaction did not exceed 60° C. When the addition was complete, the 1-isopropylsulfonamyl-2-amino-6-benzoyl-7-pyridoimidazole (0.344 g, 1 mmol), dissolved in 10 ml of tetrahydrofuran, was slowly added via cannula to the reaction mixture. When the addition was complete the solution was allowed to warm to 25° C. and then to stir for 18 hours. The reaction was quenched with 4 ml of 1N hydrochloric acid. The organic solvents were removed in vacuo and the residue taken up in acetonitrile. The crude solution was purified by reverse phase chromatography to give 44 mg of cis product (23.5%), MS(FD) m/e 399, IR—3450, 1643, 1582 cm$^{-1}$ and 50 mg of trans product. (26.7%), MS(FD) m/e 399, IR—3454, 1653, 1630 cm$^{-1}$.

Example 8

1-Isopropylsulfonamyl-2-amino-6-(1-phenyl-2-cis-carboxamyl)ethylenyl-7-pyridoimidazole

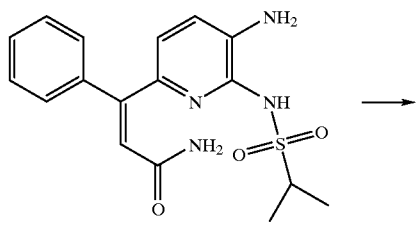

-continued

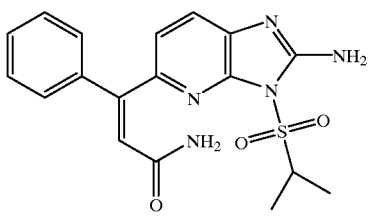

The 2-isopropylsulfonamyl-3-amino-6-(1-phenyl-2-cis-carboxamyl)ethylenylpyridine (0.130 g, 0.36 mmol) was dissolved in 5 ml of methanol and 0.5 ml of water. The cyanogen bromide (0.191 g, 1.8 mmol) was added and the mixture allowed to stir for 48 hours at 25° C. The reaction was concentrated in vacuo and the residue diluted to 10 ml with acetonitrile/water. The crude product was purified by reverse phase chromatography to give 15 mg of cis product. (11%) MS(FD) m/e 385.

Example 9

1-Isopropylsulfonamyl-2-amino-6-cis-(3-fluoro)benzoxime-7-pyridoimidazole

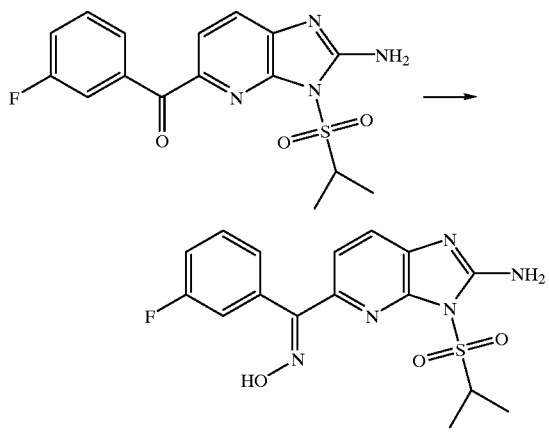

The 1-isopropylsulfonamyl-2-amino-6-(3-fluorobenzoyl)-7-pyridoimidazole (1.0 g, 2.8 mmol), hydroxylamine hydrochloride, pyridine, and methanol were combined and heated at 40° C. for 3 hours. The reaction was allowed to cool to 25° C. over 18 hours. The cis product precipitate that had formed was collected by filtration. The filtrate was concentrated in vacuo and diluted with methanol and more cis product precipitated immediately. This material was collected by filtration. The combined precipitates weighed 670 mg. (63.2%). MS(FD) m/e 377.2. Anal Calcd for $C_{16}H_{16}FN_5O_3S$: C, 50.92; H, 4.27; N, 18.56. Found: C, 51.08; H, 4.22; N, 18.55.

Example 10

1-Isopropylsulfonamyl-2-amino-6-(1-[3-fluorophenyl])ethlenyl-7-pyridoimidazole

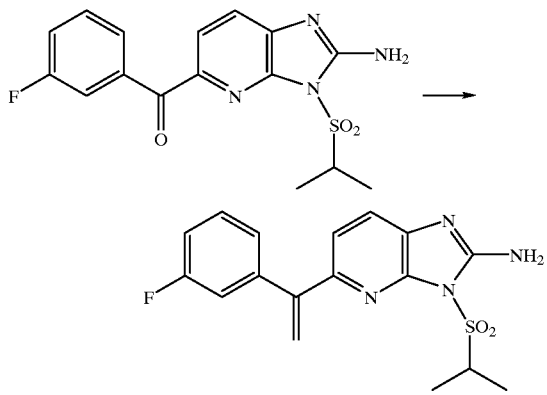

Trimethylsilylmethylmagnesium chloride, 1M solution in ether, (2.28 g, 15.5 mmol) was dissolved in 35 ml of tetrahydrofuran and chilled to 0° C. The 1-isopropylsulfonamyl-2-amino-6-(3-fluorobenzoyl)-7-pyridoimidazole (1.12 g, 3.10 mmol) was dissolved in 20 ml of tetrahydrofuran and cannulated into the Grignard solution. The mixture was allowed to warm to 25° C. HPLC showed starting material still present so an additional 0.74 g (5 mmol) of the Grignard reagent was added and the solution was stirred for 72 hours. The reaction was quenched with 5N hydrochloric acid (about 7.5 ml). The mixtures was partitioned between water and ethyl acetate. The organic layer was dried over magnesium sulfate, filtered, and concentrated in vacuo. The residue was taken up in 15% acetone:methylene chloride and the crude intermediate was purified by normal phase chromatography to yield 0.50 g of product. (45%). MS(FD) m/e 360.

Example 11

1-Isopropylsulfonamyl-2-amino-6-(1-[3-fluorophenyl]-2-cis-bromo)ethlenyl-7-pyridoimidazole

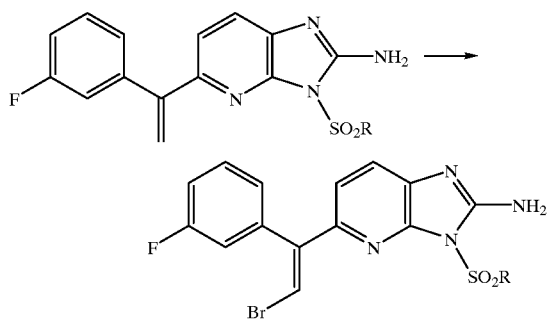

The 1-isopropylsulfonamyl-2-amino-6-(1-[3-fluorophenyl]) ethlenyl-7-pyridoimidazole (0.512 g, 1.42 mmol) was dissolved in 2.6 ml of tetrahydrofuran and 2.6 ml of carbon tetrachloride. The solution was chilled to −10° C. Bromine (0.249 g, 1.56 mmol), dissolved in 1.6 ml of carbon tetrachloride, was cannulated into the reaction mixture, and the resulting solution was allowed to stir until it warmed to 25° C. and then 1 hour at 25° C. The solution was diluted with 50 ml of methylene chloride and washed with a mixture of 10% aqueous sodium sulfite and saturated aqueous sodium bicarbonate. The organic phase was washed with brine, dried over magnesium sulfate, filtered, and concentrated in vacuo. The residue was triturated with a few ml of acetone and filtered. The filtrate was concentrated in vacuo and triturated with acetone and again filtered. Final yield of filtered cis product was 0.270 g. (19.9%). $^1$H NMR (300 MHz, DMSO-$d_6$) δ 7.61 (s, 1 H), 7.55 (q, 1 H), 7.48 (1, 1 H), 7.39 (s, 2 H), 7.28 (t, 1 H), 7.13 (t, 2 H), 6.88 (d, 1 H), 4.18 (p, 1 H), 1.32 (d, 6 H). IR—3509, 3396, 2988, 1638, 1593 cm$^{-1}$.

Example 12

1-Isopropylsulfonamyl-2-amino-6-(1-[3-fluorophenyl]-2-cyano)ethlenyl-7-pyridoimidazole

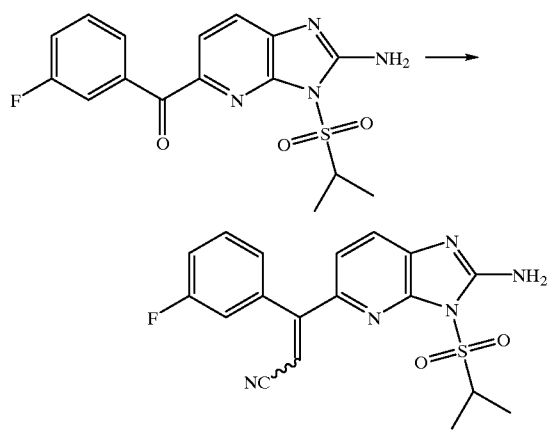

The trimethylsilylmethylcyanide (2.26 g, 20.0 mmol) was dissolved in 150 ml of tetrahydrofuran and chilled to −78° C. The n-butyl lithium (1.28 g, 20.0 mmol) was added so that the temperature of the reaction did not exceed −70° C. The 1-isopropylsulfonamyl-2-amino-6-(1-[3-fluorophenyl]) ethlenyl-7-pyridoimidazole (1.45 g, 4.00 mmol), dissolved in 20 ml of tetrahydrofuran, was slowly cannulated into the reaction mixture. After the addition was complete, the solution was allowed to warm for a few minutes and was then quenched with 20 ml of 1N hydrochloric acid. The organics solvents were removed in vacuo and the residue was diluted with pH 7 buffer. The pH of the solution was then adjusted to 5 with 5N hydrochloric acid. The aqueous phase was extracted with ethyl acetate. The ethyl acetate was then dried over magnesium sulfate, filtered, and concentrated in vacuo. The residue was triturated with ethyl ether and filtered to give 130 mg of an approximately 60:40 cis:trans product mixture. (84%). MS(FD) m/e 385.1. IR—3508, 3394, 2215, 1640, 1602, 1577 cm$^{-1}$.

Example 13

1-Isopropylsulfonamyl-2-amino-6-(1-[3-fluorophenyl]-2-methylcarboxamyl)ethlenyl-7-pyridoimidazole

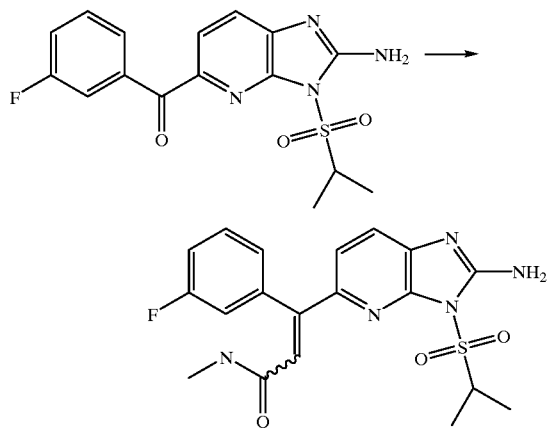

The Peterson Reagent (from Preparation 14) (1.08 g, 5.00 mmol) was dissolved in tetrahydrofuran in a flame dried flask and chilled to −78° C. The n-butyl lithium (2.5 ml, 4 mmol) was added slowly via syringe so that the temperature of the reaction did not exceed −55° C. When the addition was complete, the solution was allowed to equilibrate back to −78° C. and the 1-isopropylsulfonamyl-2-amino-6-(1-[3-fluorophenyl])ethlenyl-7-pyridoimidazole (0.362 g, 1.00 mmol), dissolved in 10 ml of tetrahydrofuran, was slowly cannulated into the reaction mixture. When the addition was complete the reaction was allowed to warm to 25° C. The reaction was quenched with 4 ml of 1N hydrochloric acid. The organic solvents were removed in vacuo and then acetonitrile was added. A colorless layer separated out on the bottom and was removed. The remaining material was diluted to 8 ml with acetonitrile and the crude product was purified by reverse phase chromatography to yield 46 mg of cis product. $^1$H NMR (300 MHz, DMSO-$d_6$) δ 7.42 (d, 1 H), 7.28–7.41 (m, 3 H), 7.15 (t, 1 H), 6.85–7.0 (m, 3 H), 6.8 (d, 1 H), 4.18 (p, 1 H), 2.55 (d, 3 H) 1.35 (d, 6 H) and 28 mg of trans product. MS(FD) 417. IR—3459, 1654, 1632, 1593, 1582 cm$^{-1}$.

As described above, the compounds of the present invention are useful as antiviral agents. They show inhibitory activity against various strains of enterovirus and rhinovirus. An embodiment of the present invention is a method of treating or preventing picornaviridae infection comprising administering to a host in need thereof an effective amount of a compound of Formula (I) or a pharmaceutically acceptable salt thereof.

The term "effective amount" as used herein, means an amount of a compound of Formula (I) which is capable of inhibiting viral replication. The picornaviridae inhibition contemplated by the present method includes either therapeutic or prophylactic treatment, as appropriate. The specific dose of compound administered according to this invention to obtain therapeutic or prophylactic effects will, of course, be determined by the particular circumstances surrounding the case, including, for example, the compound administered, the route of administration, the condition being treated and the individual being treated. A typical daily dose will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of Formula (I) or a pharmaceutically acceptable salt thereof and a pharmaceutically acceptable carrier, diluent or excipient thereof.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

The present pharmaceutical formulations are prepared by known procedures using well-known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

The following formulation example is only illustrative and is not intended to limit the scope of the invention in any way.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Test Methods

African green monkey kidney cells (BSC-1) or Hela cells (5-3) were grown in 25 cc Falcon flasks at 37° C. in medium 199 with 5 percent inactivated fetal bovine serum (FBS), penicillin (150 units 1 ml) and streptomycin (150 micrograms per milliliter (μg/ml)). When confluent monolayers were formed, the supernatant growth medium was removed and 0.3 ml of an appropriate dilution of virus (e.g. echo, Mengo, Coxsackie, polio or rhinovirus) were added to each flask. After absorption for one hour at room temperature, the virus infected cell sheet was overlaid with a medium comprising one part of 1 percent Ionagar No. 2 and one part double strength medium 199 with FBS, penicillin and streptomycin which contains drug at concentrations of 100, 50, 25, 12, 6, 3 and 0 μg/ml. The flask containing no drug served as the control for the test. The stock solutions of compounds were diluted with dimethylsulfoxide to a concentration of $10^4$ μg/ml. The flasks were then incubated for 72 hours at 37° C. for polio, Coxsackie, echo and Mengo virus and 120 hours at 32° C. for rhinovirus. Virus plaques were seen in those areas were the virus infected and reproduced in the cells. A solution of 10 percent formalin and 2 percent sodium acetate was added to each flask to inactivate the virus and fix the cell sheet to the surface of the flask. The virus plaques, irrespective of size, were counted after staining the surrounding cell areas with crystal violet. The plaque count was compared to the control count at each drug concentration. The activity of the test compound can be expressed as percentage plaque reduction, or percent inhibition. Alternatively, the drug concentration which inhibits plaque formation by 50 percent can be used as a measure of activity. The 50 percent inhibition value is denoted as the "$IC_{50}$". The compounds of the present invention displayed at least 30%, preferably 50% and most preferably over 85% inhibition of plaque formation at a single dose of 50 μmol. Dose response titrations on the compounds of the present invention reveal $IC_{50}$ values of <10 μM,.

We claim:

1. A compound of the Formula (I):

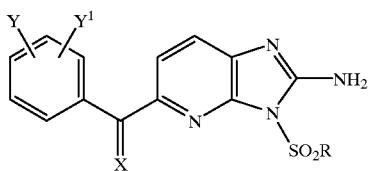

(I)

wherein:

R is $C_1$–$C_6$ alkyl, phenyl, or phenyl substituted with halo, $C_1$–$C_4$ alkyl or trifluoromethyl;

Y and $Y^1$ are independently hydrogen, halo, or triflouromethyl;

X is N—OH, O, or $CHR^1$;

$R^1$ is hydrogen, halo, CN, $C_1$–$C_4$ alkyl, —C≡CH, $CONR^2R^3$, $COR^2$, or $CO_2R^2$;

$R^2$ and $R^3$ are independently hydrogen or $C_1$–$C_4$ alkyl;

or a pharmaceutiacally acceptable salt thereof.

2. A compound of claim 1 wherein:

R is phenyl or isopropyl; and

Y and $Y^1$ are independently hydrogen or halo.

3. A compound of claim 2 wherein:

X is $CHR^1$; and $R^1$ is hydrogen, halo, CN, $CONR^2R^3$.

4. A compound of claim 3 wherein:

Y and $Y^1$ are both fluoro; and

R is isopropyl.

5. A compound of claim 4 wherein:

$R^1$ is $CONR^2R^3$;

$R^2$ is hydrogen, methyl, or ethyl; and $R^3$ is methyl or ethyl.

6. A pharmaceutical formulation comprising, a compound of claim 1, or a pharmaceutically acceptable salt thereof, in combination with one or more pharmaceutically acceptable carriers.

7. A method for inhibiting a picornavirus comprising administering to a host in need thereof a picornavirus inhibiting amount of a compound of claim 1.

8. The method of claim 7 wherein the picornavirus is a rhinovirus.

* * * * *